(12) United States Patent
Torrence et al.

(10) Patent No.: US 9,567,282 B2
(45) Date of Patent: *Feb. 14, 2017

(54) PRODUCTION OF ACETIC ACID WITH HIGH CONVERSION RATE

(71) Applicant: Celanese International Corporation, Irving, TX (US)

(72) Inventors: G. Paull Torrence, League City, TX (US); Brian W. Hokkanen, Houston, TX (US); Michael O. Nutt, Pearland, TX (US); Tianshu Pan, Houston, TX (US); Ronald D. Shaver, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 812 days.

This patent is subject to a terminal disclaimer.

(21) Appl. No.: 13/780,040

(22) Filed: Feb. 28, 2013

(65) Prior Publication Data

US 2013/0172614 A1 Jul. 4, 2013

Related U.S. Application Data

(62) Division of application No. 12/892,348, filed on Sep. 28, 2010, now Pat. No. 8,394,988.

(51) Int. Cl.
*C07C 51/12* (2006.01)
*C07C 51/44* (2006.01)
*B01J 19/00* (2006.01)

(52) U.S. Cl.
CPC ............... *C07C 51/12* (2013.01); *B01J 19/00* (2013.01); *C07C 51/44* (2013.01)

(58) Field of Classification Search
CPC .................................................... C07C 51/12
USPC ................................................. 562/519, 517
See application file for complete search history.

(56) References Cited

U.S. PATENT DOCUMENTS

| | | |
|---|---|---|
| 3,769,329 A | 10/1973 | Knox et al. |
| 4,994,608 A | 2/1991 | Torrence et al. |
| 5,001,259 A | 3/1991 | Smith et al. |
| 5,026,908 A | 6/1991 | Smith et al. |
| 5,144,068 A | 9/1992 | Smith et al. |
| 5,334,755 A | 8/1994 | Yoneda et al. |
| 5,380,929 A | 1/1995 | Erpenbach et al. |
| 5,391,821 A | 2/1995 | Koyama et al. |
| 5,599,976 A | 2/1997 | Scates et al. |
| 5,672,744 A | 9/1997 | Kagotani et al. |
| 5,683,492 A | 11/1997 | Hesse et al. |
| 5,696,284 A | 12/1997 | Baker et al. |
| 5,731,252 A | 3/1998 | Warner et al. |
| 5,840,969 A | 11/1998 | Joensen |
| 5,877,347 A | 3/1999 | Ditzel et al. |
| 5,877,348 A | 3/1999 | Ditzel et al. |
| 5,883,295 A | 3/1999 | Sunley et al. |
| 5,883,764 A | 3/1999 | Pinarbasi |
| 5,917,089 A | 6/1999 | Howard |
| 5,932,764 A | 8/1999 | Morris et al. |
| 5,942,460 A | 8/1999 | Garland et al. |
| 6,140,535 A | 10/2000 | Williams |
| 6,143,930 A | 11/2000 | Singh et al. |
| 6,153,792 A | 11/2000 | Leet et al. |
| 6,232,352 B1 | 5/2001 | Vidalin |
| 6,339,171 B1 | 1/2002 | Singh et al. |
| 6,462,231 B1 | 10/2002 | Yanagawa et al. |
| 6,617,471 B2 | 9/2003 | Zoeller et al. |
| 6,627,770 B1 | 9/2003 | Cheung et al. |
| 6,657,078 B2 | 12/2003 | Scates et al. |
| 6,727,380 B2 | 4/2004 | Ellis et al. |
| 7,005,541 B2 | 2/2006 | Cheung et al. |
| 7,052,657 B2 | 5/2006 | Nakajima |
| 7,115,772 B2 | 10/2006 | Picard et al. |
| 7,202,382 B2 | 4/2007 | Muskett |
| 7,208,624 B2 | 4/2007 | Scates et al. |
| 7,223,886 B2 | 5/2007 | Scates et al. |
| 7,473,800 B2 | 1/2009 | Hosono et al. |
| 7,678,940 B2 | 3/2010 | Miura et al. |
| 2003/0199711 A1 | 10/2003 | Broussard et al. |
| 2005/0165251 A1 | 7/2005 | Muskett |
| 2008/0287706 A1 | 11/2008 | Powell et al. |
| 2008/0293966 A1 | 11/2008 | Scates et al. |
| 2008/0293996 A1 | 11/2008 | Evans et al. |

(Continued)

FOREIGN PATENT DOCUMENTS

| | | |
|---|---|---|
| CN | 1537840 | 10/2004 |
| CN | 101439256 | 5/2009 |

(Continued)

OTHER PUBLICATIONS

J. Jones, et al., Platinum Metals Review, vol. 44, No. 3, pp. 94-104 (Jul. 2000).
Yoneda, et al., "Acetic Acid Process Catalyzed by Ionically Immobilized Rhodium Complex to Solid Resin Support", 2004, Journal of Chemical Engineering of Japan, vol. 34, No. 4, pp. 536-545.
Gaub, et al., Applied Homogeneous Catalysis with Organometallic Compounds: A Comprehensive Handbook in Two Volumes, Chapter 2.1, pp. 27-200, (1$^{st}$. Ed., 1996).
International Search Report and Written Opinion for PCT/US2011/053369 dated Feb. 9, 2012.
International Search Report and Written Opinion for PCT/US2011/053539 dated Jan. 25, 2011.

(Continued)

*Primary Examiner* — Yevegeny Valenrod
(74) *Attorney, Agent, or Firm* — Kilpatrick Townsend & Stockton LLP

(57) ABSTRACT

A process for producing acetic acid comprising the steps of reacting carbon monoxide and at least one of methanol and a methanol derivative in a first reactor under conditions effective to produce a crude acetic acid product; separating the crude acetic acid product into at least one derivative stream, at least one of the at least one derivative stream comprising residual carbon monoxide; and reacting at least a portion of the residual carbon monoxide with at least one of methanol and a methanol derivative over a metal catalyst in a second reactor to produce additional acetic acid.

13 Claims, 5 Drawing Sheets

(56) References Cited

U.S. PATENT DOCUMENTS

| | | |
|---|---|---|
| 2009/0107833 A1 | 4/2009 | Warner |
| 2009/0270650 A1 | 10/2009 | Patt |
| 2009/0270651 A1 | 10/2009 | Zinobile et al. |
| 2010/0069514 A1 | 3/2010 | Gracey et al. |

FOREIGN PATENT DOCUMENTS

| | | |
|---|---|---|
| EP | 2 093 209 A1 | 8/2009 |
| JP | 4-70245 B2 | 11/1992 |
| JP | 6-340242 | 12/1994 |
| JP | 8-188547 | 7/1996 |
| JP | 2011-512391 A | 4/2011 |
| WO | WO 2007/107724 | 9/2007 |
| WO | WO 2012/050846 | 4/2012 |

OTHER PUBLICATIONS

Examination Report for corresponding Pakistan Appl. No. 706/2011 dated Jan. 2, 2013.
Office Action for corresponding U.S. Appl. No. 12/892,348 dated Dec. 14, 2012.
Response to Office Action for corresponding U.S. Appl. No. 12/892,348 filed Jan. 7, 2013.
Notice of Allowance for corresponding U.S. Appl. No. 12/892,348 dated Jan. 24, 2013.
International Search Report and Written Opinion for PCT/US2012/052829 mailed Feb. 6, 2013.

PRODUCTION OF ACETIC ACID WITH HIGH CONVERSION RATE

This application is a divisional of U.S. patent application Ser. No. 12/892,348, filed Sep. 28, 2010, which issued on Mar. 12, 2013 as U.S. Pat. No. 8,394,988, the entirety of which is hereby incorporated by reference.

FIELD OF THE INVENTION

This invention relates to processes for producing acetic acid from carbon monoxide and, in particular, to improved processes, which react residual carbon monoxide to form additional acetic acid, thus improving the overall conversion of the carbon monoxide feed.

BACKGROUND OF THE INVENTION

A widely used and successful commercial process for synthesizing acetic acid involves the catalyzed carbonylation of methanol with carbon monoxide. The catalysis contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105, the entire content and disclosure of which is hereby incorporated by reference.

During the methanol carbonylation reaction, by-product gases build up in the reactor as the crude acetic acid product is withdrawn into a flasher. The build-up of these gases in the reactor is often controlled by venting an off-gas from the reactor to keep the carbon monoxide partial pressure in the reactor at an acceptable level to maximize catalyst activity and stability. The vented off-gas may comprise carbon monoxide, inert and by-product gases, volatile halogen promoters, acetic acid, water, unreacted methanol, and/or methyl acetate. In most methanol carbonylation processes the off-gas is processed in one or more recovery units to recover volatile halogen promoters, acetic acid, water, unreacted methanol, and/or methyl acetate and return those recovered compounds to the reactor. The gases that pass out of the recovery units may be purged and/or directed to a flasher vessel to enhance catalyst stability. An example of a recovery unit is described in U.S. Pub. Nos. 2008/0293996 and 2009/0270651, the entire contents and disclosure of which are hereby incorporated by reference.

U.S. Pat. No. 5,917,089 discloses that an "off-gas" from the reactor may be fed directly to a second reactor, along with fresh methanol, to produce additional carbonylation product, i.e. acetic acid. The off-gas, as known in the art, however, is not a derivative stream.

A purification section processes the crude acetic acid product from the reactor to remove impurities thus providing a high quality acetic acid product. These impurities, which may be present in trace amounts, affect the quality of acetic acid, especially as the impurities are circulated through the reaction process, which, among other things, can result in the build up over time of these impurities. Conventional purification techniques to remove these impurities include treating the acetic acid product streams with oxidizers such as ozone, reducers such as hydrogen, water, methanol, activated-carbon, amines, and the like. The treatments may or may not be combined with the distillation of the crude acetic acid product. Typically, during the purification, there are several vents, which purge non-condensable gases formed in the reactor. The vented gases may be processed in a recovery unit to recover light boiling point components, such as the halogen promoter, as described in U.S. Pub. No. 2008/0293966, the entire content and disclosure of which is hereby incorporated by reference. The vented gases, which also contain carbon monoxide, that pass through the recovery unit are typically purged or flared. The loss of the carbon monoxide represents a loss of the reactants.

An alternative to the liquid-phase methanol carbonylation process is described in U.S. Pat. No. 6,617,471, the entire contents and disclosures of which are hereby incorporated by reference. U.S. Pat. No. 6,617,471 discloses a vapor-phase carbonylation method for producing esters and carboxylic acids from reactants comprising lower alkyl alcohols, lower alkyl alcohol generating compounds, and mixtures thereof. The method includes contacting the reactants and carbon monoxide in a carbonylation zone of a carbonylation reactor under vapor-phase conditions with a catalyst having a catalytically effective amount of iridium and tin associated with a solid carrier material.

In view of these references, the need exists for a process for processing vented gases during the purification and separation of the crude acetic acid product to recover reactants and improve the efficiency of the acetic acid production.

SUMMARY OF THE INVENTION

The present invention is to processes for producing acetic acid. In a first embodiment, a process comprises the step of reacting carbon monoxide and at least one of methanol and a methanol derivative in a first reactor under conditions effective to produce a crude acetic acid product. The crude acetic acid product comprises acetic acid and residual carbon monoxide. The process further comprises separating the crude acetic acid product into at least one derivative stream. The derivative stream(s) comprise residual carbon monoxide. The process further comprises the step of reacting at least a portion of the residual carbon monoxide with at least one of methanol and a methanol derivative, preferably methyl acetate, over a metal catalyst in a second reactor to produce additional acetic acid. Preferably, the second reactor is a trickle bed reactor or a fixed bed reactor and the metal catalyst in the second reactor comprises at least one metal selected from the group consisting of rhodium, iridium, ruthenium, nickel, and cobalt. In a preferred aspect, the overall conversion of carbon monoxide is greater than 90%.

In another embodiment, a process comprises the step of contacting a carbonylation reaction stream and/or a derivative thereof with at least one of methanol and a methanol derivative over a metal catalyst to produce an acetic acid composition. Preferably, the carbonylation reaction stream and/or derivative thereof comprises a low amount of carbon monoxide, e.g., from 10 mol % to 95 mol % carbon monoxide. In one aspect, the carbonylation reaction stream and/or derivative thereof has been separated to remove condensable liquids. In another aspect, the resultant product stream comprises less than 40 mol % carbon monoxide.

In another embodiment, a process comprises the step of contacting a carbon monoxide feed and at least one of methanol and a methanol derivative under conditions effective to produce a reaction product. The reaction product comprises a crude acetic acid product and a vent stream. The vent stream comprises a low amount of carbon monoxide, e.g., less than 60 mol % carbon monoxide.

In another embodiment, a process comprises the step of contacting a carbon monoxide feed stream comprising carbon monoxide and having a carbon monoxide partial pressure of less than 95% of the total pressure of the carbon monoxide feed stream with at least one of methanol and a methanol derivative over a solid phase metal catalyst to produce an acetic acid composition. Preferably, the carbon monoxide feed stream is a carbonylation reaction product stream or a derivative thereof.

In another embodiment, the invention is to a system for producing acetic acid. The system comprises a first reactor, a second reactor, and a separator. The first reactor reacts carbon monoxide and at least one of methanol and a methanol derivative to produce a crude acetic acid product. The separator separates the crude acetic acid product into at least one derivative stream, which comprises residual carbon monoxide. The second reactor reacts at least a portion of the residual carbon monoxide with at least one of methanol and a methanol derivative, preferably methyl acetate, to produce additional acetic acid.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
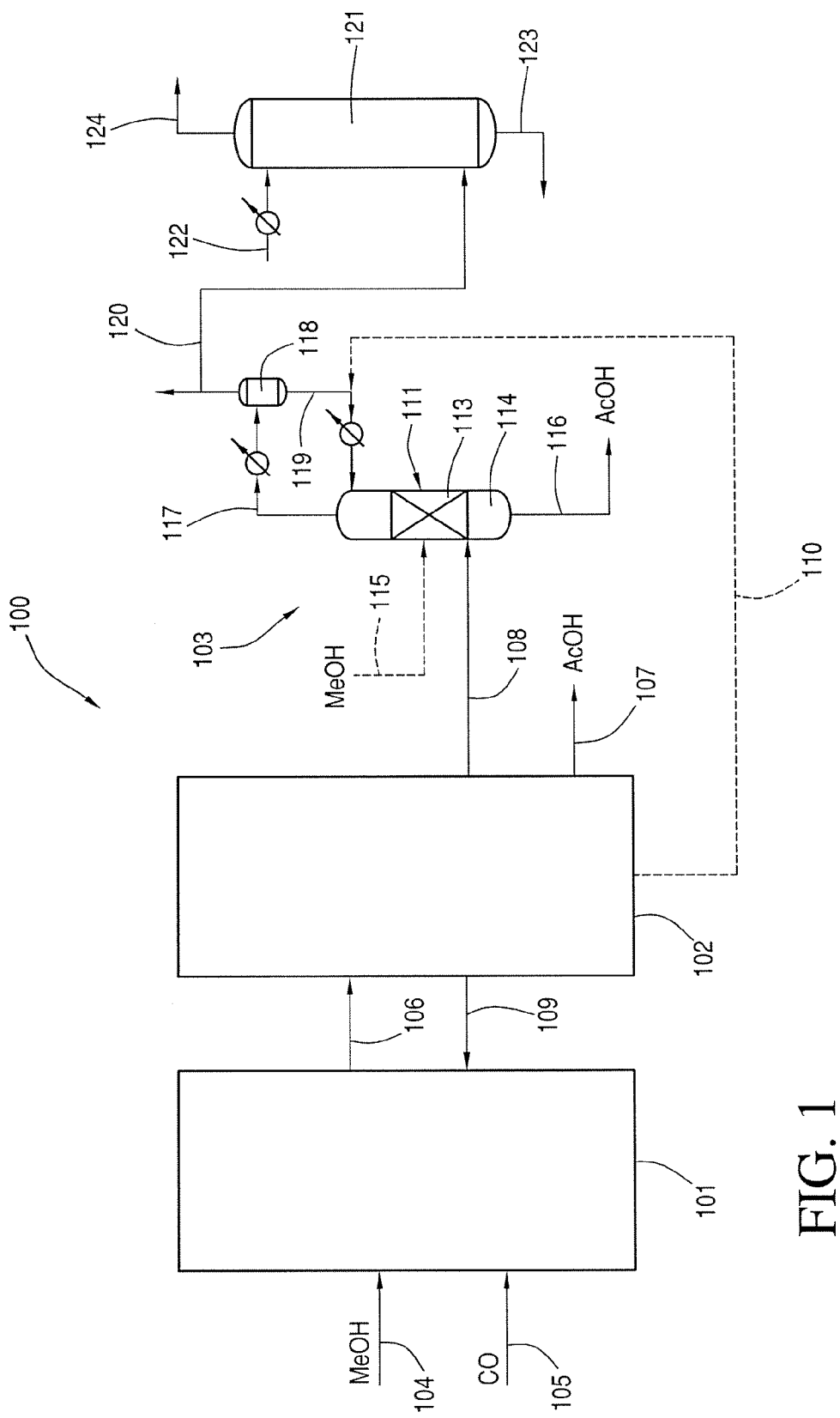
FIG. 1 is a schematic diagram of an exemplary high pressure liquid phase carbonylation secondary reactor for processing a purged derivative stream from an acetic acid purification section in accordance with an embodiment of the present invention.

The present invention generally relates to producing acetic acid from residual or unreacted carbon monoxide that is present in derivative streams of a crude acetic acid product. The derivative streams are obtained during the purification and separation of the crude acetic acid product. For purposes of the present application, the separation zone refers to the portion of the process that purifies or separates the crude acetic acid product. In a preferred embodiment, the derivative streams are vented gas streams of the separation zone. In one embodiment, the present invention advantageously increases the overall carbon monoxide efficiency by utilizing the residual carbon monoxide in the derivative streams to form additional acetic acid. Another embodiment of the present invention advantageously reduces the amount of carbon monoxide that is purged or flared from the purification and separation section.

The present invention, in one embodiment, relates to a process for producing acetic acid comprising the step of reacting carbon monoxide and methanol and/or a methanol derivative in a first reactor under conditions effective to produce a crude acetic acid product. The crude acetic acid product comprises acetic acid and residual carbon monoxide. The residual carbon monoxide may be dissolved and/or entrained in the crude acetic acid product. In one embodiment, the crude acetic acid product comprises residual carbon monoxide in an amount less than 20 mol %, e.g., less than 10 mol %, less than 5 mol %, or less than 3 mol %. In another embodiment, a flashed vapor phase crude acetic acid product has a carbon monoxide partial pressure that is less than 20% of the total pressure of the flashed crude acetic acid product, e.g., less than 10%, less than 5%, or less than 3%. In another embodiment, the flashed crude acetic acid product is at a total pressure of 0.3 MPa has a carbon monoxide partial pressure of less than 0.06 MPa, e.g., less than 0.03 MPa; less than 0.015 MPa; or less than 0.009 MPa. Of course, for carbon monoxide to be reacted with methanol and/or a methanol derivative to form additional acetic acid, some amount of carbon monoxide should be present. For example, the crude acetic acid product may comprise residual carbon monoxide in an amount greater than 0.1 mol %, greater than 0.5 mol % or greater than 1 mol %. In terms of partial pressures, the flashed crude acetic acid product may have a (residual) carbon monoxide partial pressure of at least 0.1% of the total pressure of the flashed crude acetic acid product, e.g., at least 0.5% or at least 1%. For example, where the flashed crude acetic acid product is at 0.3 MPa total pressure, the carbon monoxide partial pressure may be of at least 0.0003 MPa, e.g., at least 0.0015 MPa or at least 0.003 MPa. In addition, the crude acetic acid product may comprise at least 50 mol % acetic acid, e.g., at least 75 mol %, at least 90 mol %, at least 95 mol %, or at least 98 mol %. In other embodiments, the crude acetic acid product may have an acetic acid partial pressure of at least 50% of the total pressure of the crude acetic acid product, e.g., at least 75%, at least 90%, at least 95%, or at least 98%. In terms of ranges, the crude acetic acid product optionally comprises from 0.1 mol % to 20 mol % residual carbon monoxide, e.g., from 0.5 mol % to 10 mol %, or from 1 mol % to 5 mol %; or from 50 mol % to 99.9 mol % acetic acid, e.g., from 60 mol % to 99 mol %, or from 75 mol % to 95 mol %. In terms of partial pressures, the crude acetic acid product optionally has a carbon monoxide partial pressure of from 0.1% to 20% of the total pressure of the crude acetic acid product, e.g., from 0.5% to 10% or from 1% to 5%; and an acetic acid partial pressure of from 50% to 99.9% of the total pressure of the crude acetic acid product, e.g., from 60% to 99% or from 75% to 95%. Optionally, the crude acetic acid product further comprises methyl iodide (liquid and/or vapor), methyl acetate, propionic acid, water, residual catalyst, and acetaldehyde. In one embodiment, the crude acetic acid product may comprise acetic acid, residual catalyst, dissolved and/or entrained carbon monoxide, methyl iodide, methyl acetate, water, permanganate reducing compounds ("PRCs"), and/or other dissolved gases such as carbon dioxide, hydrogen, and methane.

The process further comprises the step of separating the crude acetic acid product into a plurality of derivative streams. At least one of the derivative streams, e.g., at least two or at least three of the derivative streams, comprises at least a portion of the residual carbon monoxide. Preferably, the at least one of the derivative streams is a vapor. Residual carbon monoxide, e.g., unreacted carbon monoxide, includes carbon monoxide that has not reacted in the carbonylation reaction and, as such, remains in the crude acetic acid product. In one embodiment, the residual carbon monoxide in the derivative stream(s) is entrained in the respective stream. Without being bound by theory, it is believed that the entrainment of the carbon monoxide is due to the carbon monoxide being conveyed through the liquid reaction mixture. In contrast, a typical off-gas stream is simply a stream that is removed from the vapor built up in the reactor. Thus the carbon monoxide in conventional off-gas streams is not entrained in the stream. In one embodiment, the derivative stream(s) comprise less carbon monoxide than the carbon monoxide fed to the primary reactor. In one embodiment, the derivative stream(s) comprise less than 95 mol % carbon monoxide, e.g., less than 80 mol %, less than 75 mol %, less than 60 mol %, less than 50 mol %, or less than 40 mol %. In another embodiment, the vapor phase derivative stream(s) have a carbon monoxide partial pressure of less than 95% of the total pressure of the vapor phase derivative stream(s), e.g., less than 75%, less than 60%, less than 50%, or less than 40%. In terms of ranges, the derivative stream(s) optionally comprise from 10 mol % to 95 mol % residual carbon monoxide, e.g., from 25 mol % to 75 mol %, or from 40 mol % to 60 mol %. Preferably, the derivative stream(s) comprise from 60 mol % to 70 mol % carbon monoxide. In terms of partial pressures, the derivative stream(s) optionally have a carbon monoxide partial pressure of from 10% to 95% of the total pressure of the derivative stream(s), e.g., from 25% to 75% or from 40% to 60%. In addition, the process comprises the step of reacting, in a second reactor, at least a portion of the residual carbon monoxide from one or more of the derivative streams, with methanol and/or a methanol derivative, e.g., methyl acetate or dimethyl ether, to produce additional acetic acid. The reaction in the second reactor is preferably performed in a fixed bed reactor or a trickle bed reactor. These reactors preferably comprise a catalyst, e.g., a solid phase metal catalyst. The second reactor provides for reaction of residual carbon monoxide, which improves overall process efficiency.

In another embodiment, the invention relates to a process for producing acetic acid comprising the step of contacting with at least one of methanol and a methanol derivative a carbon monoxide feed stream, e.g., a low carbon monoxide content feed stream, comprising a low concentration of carbon monoxide (as compared to conventional carbon monoxide feed streams), e.g., from 10 mol % to 95 mol %, from 25 mol % to 75 mol % or from 40 mol % to 60 mol % carbon monoxide. Preferably, the low carbon monoxide content feed stream comprises from 60 mol % to about 70 mol % carbon monoxide. In terms of partial pressures, the low carbon monoxide content feed streams optionally have a carbon monoxide partial pressure of from 10% to 95% of the total pressure of the derivative stream(s), e.g., from 25% to 75% or from 40% to 60%. In terms of limits, the low carbon monoxide feed stream preferably comprises less than 95 mol % carbon monoxide, e.g., less than 80 mol %, less than 70 mol %, less than 50 mol %, or less than 40 mol %. In other embodiments, the low carbon monoxide feed stream has a carbon monoxide partial pressure less than 95% of the total pressure of the low carbon monoxide feed stream, e.g., less than 80%, less than 70%, less than 50%, or less than 40%. Again, for carbon monoxide to be reacted with methanol to form acetic acid, some amount of carbon monoxide should be present in the carbon monoxide feed stream. For example, the carbon monoxide feed stream may comprise residual carbon monoxide in an amount greater than 0.1 mol %, greater than 0.5 mol % or greater than 1 mol %; or the carbon monoxide feed stream may have a carbon monoxide partial pressure greater than 0.1% of the total pressure of the low carbon monoxide feed stream, e.g., greater than 0.5% or greater than 1%. The carbon monoxide feed stream may further comprise, for example, methanol and/or a methanol derivative, e.g., methyl acetate or dimethyl ether, which is used to produce an acetic acid composition. The inventive process reacts low carbon monoxide feed streams, optionally obtained from vented gases, and thus avoids the waste thereof. Preferably, the contacting step is performed in a fixed bed reactor or a trickle bed reactor and over a catalyst, e.g., a solid phase metal catalyst, which may be fixed in a catalyst bed. The catalyst may be specifically selected for use with the low concentration carbon monoxide feed stream.

In another embodiment, the invention is to a process for producing acetic acid comprising the step of contacting a carbon monoxide feed stream having a carbon monoxide partial pressure of less than 95% of the total pressure the carbon monoxide feed stream, e.g., less than 90%, less than 80%, less than 70%, less than 50%, or less than 40%, with at least one of methanol and a methanol derivative to produce an acetic acid composition. Thus, this embodiment of the invention utilizes a feed stream having a partial pressure of carbon monoxide lower than conventional processes, e.g., at least 5% lower, at least 10% lower, at least 20% lower, or at least 50% lower. Preferably, the carbon monoxide feed stream is the reaction product of a previous carbonylation reaction or a derivative thereof, which may have been separated, for example, to remove condensable liquids. Preferably, the contacting is performed over a solid phase metal catalyst. As noted above, for carbon monoxide to be reacted with methanol to form acetic acid, some amount of carbon monoxide should be present in the carbon monoxide feed stream. Advantageously, this process has the capability to utilize carbon monoxide streams that are less pure than conventional carbon monoxide feed streams.

Also, an additional embodiment relates to a process for producing acetic acid comprising the step of contacting a carbon monoxide feed and at least one of methanol and a methanol derivative under conditions effective to produce a reaction product comprising a crude acetic acid product and a vent stream. The vent stream comprises low amounts of carbon monoxide, e.g., less than 60 mol %, e.g., less than 50 mol %, less than 25 mol %; less than 10 mol %; less than 5 mol %; or less than 1 mol %. In terms of ranges, the vent stream may comprise from 0.1 mol % to 60 mol % carbon monoxide, e.g., from 1 mol % to 50 mol %, or from 5 mol % to 25 mol %. In another embodiment, the vent stream has a carbon monoxide partial pressure less than 60% of the total pressure of the vent stream, e.g., less than 50%, less than 25%, less than 10%, less than 5%, or less than 1%. As such, less carbon monoxide is wasted through venting and the overall carbon monoxide conversion may be advantageously improved. In one embodiment, the overall carbon monoxide conversion relates to the conversion of the initial carbon monoxide feed stream in a first reaction and the conversion of residual carbon monoxide in a second reaction. Overall carbon monoxide conversions, are preferably greater than 90%, e.g., greater than 95%, greater than 99%, or greater than 99.5%.

Carbonylation

The features of the present invention may be applied to any suitable methanol carbonylation process. The formation of acetic acid via a carbon monoxide/methanol carbonylation reaction may be carried out by reacting methanol and/or methanol derivatives with carbon monoxide. Exemplary carbonylation systems 100 are shown in FIGS. 1-5. Carbonylation systems 100 comprise carbonylation reaction zone 101, separation zone 102 and a secondary reaction zone 103. Other exemplary carbonylation systems, including reaction zone and separation zones, that may be used with embodiments of the present invention include those described in U.S. Pat. Nos. 7,223,886, 7,005,541, 6,6657,078, 6,339,171, 5,731,252, 5,144,068, 5,026,908, 5,001,259, 4,994,608, and U.S. Pub. No. 2008/0287706, 2008/0293966, 2009/0107833, 2009/0270651, the entire contents and disclosures of which are hereby incorporated by reference. Exemplary reaction zone 101 and separation zone 102 are shown in the detailed schematic diagrams discussed below with respect to FIGS. 3-5.

As shown in FIGS. 1-5, methanol feed stream 104 and carbon monoxide feed stream 105 are fed, preferably continuously fed, to reaction zone 101 to produce a crude acetic acid product 106. Crude acetic acid product 106 may be fed to the separation zone 102 which produces a purified acetic acid product 107 and derivative streams 108 and 109, and optional derivative stream 110. Derivative stream 108 may be fed to secondary reaction zone 103. Derivative stream 109, which may comprise recycled compounds, may be fed to reaction zone 101. In optional embodiments, optional derivative stream 110 may also be fed to secondary reaction zone 103. In one embodiment, the derivative stream(s) are streams that are derived from the crude acetic acid product. For example, the derivative stream(s) may be streams that result from the separation of the crude acetic acid product. As another example, the derivative streams may be stream(s) yielded by flasher 131. In one embodiment, the derivative stream(s) do not include conventional off-gas streams. Conventional off-gas streams are merely streams of by-product gases that build up in the reactor as the crude acetic acid product is withdrawn, e.g., withdrawn into a flasher. These off-gas streams essentially comprise reaction by-products, and do not result from the separation of the crude acetic acid product. Thus, conventional off-gas streams are not considered to be derivative streams.

Because the present invention provides for more efficient utilization of residual carbon monoxide, the inventive processes and systems may allow larger quantities of off-gas to be withdrawn from the reactor and/or the flasher. These larger quantities may beneficially be used to supplement other streams in the system, e.g., recycle streams or pump-around streams. In conventional systems, increased off-gas withdrawal would result in increased waste of carbon monoxide.

Figure 2:
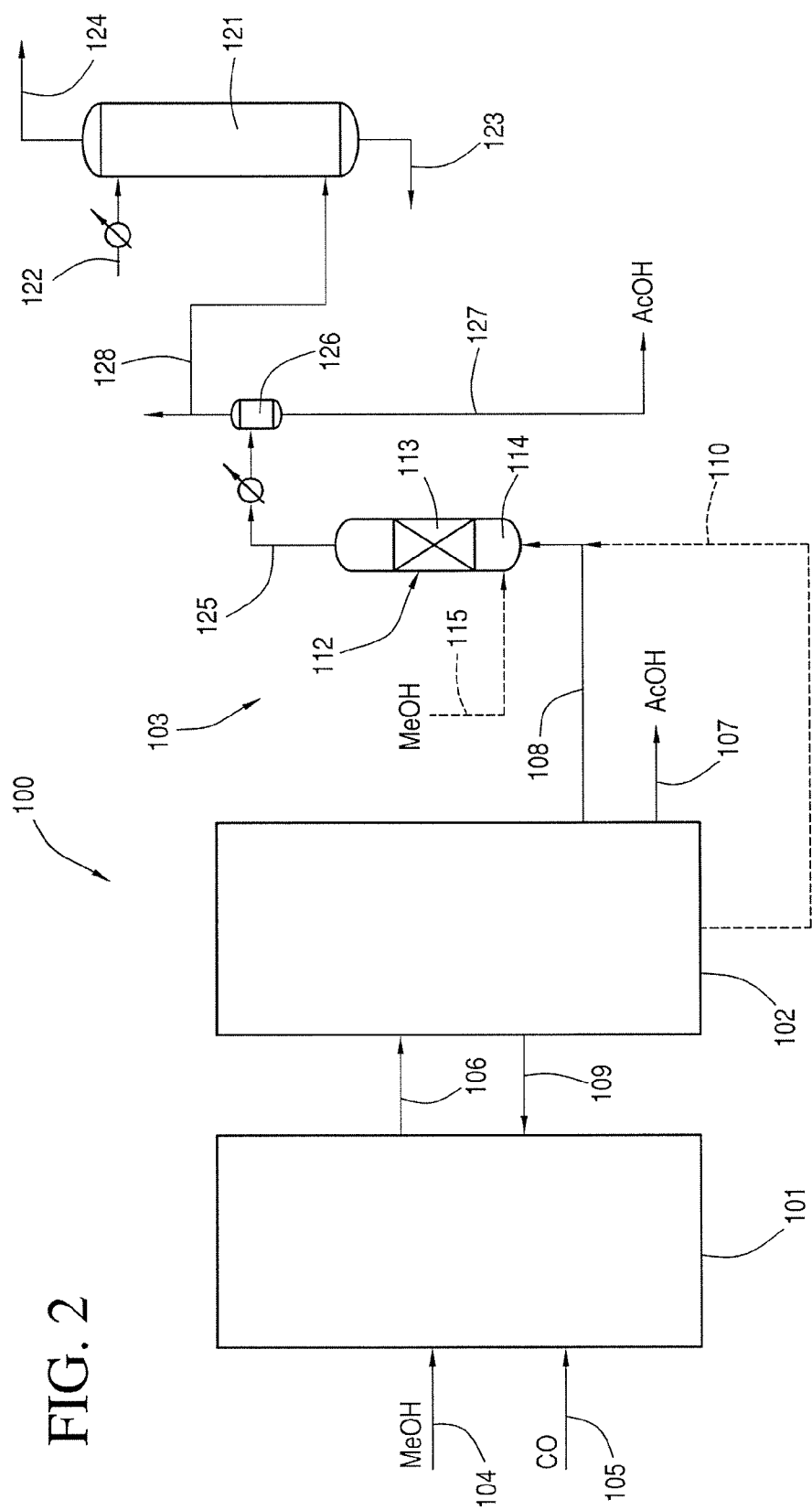
FIG. 2 is a schematic diagram of an exemplary low pressure gas phase carbonylation secondary reactor for processing a purged derivative stream from an acetic acid purification section in accordance with an embodiment of the present invention.

Derivative stream 108 may be in the liquid-phase or vapor-phase and preferably comprises dissolved and/or entrained carbon monoxide and optionally methanol and/or its reactive derivatives, preferably methyl acetate. In preferred embodiments, derivative stream 108 is in the vapor-phase. In FIG. 1, derivative stream 108 is fed to secondary reactor 111, which preferably is a high pressure liquid phase carbonylation secondary reactor. In FIG. 2, derivative stream 108 is fed to secondary reactor 112, which preferably is a low pressure gas phase carbonylation secondary reactor.

The process conditions for the supplemental carbonylation reaction in the secondary reactors 111, 112 may vary widely. The reaction may be conducted over a homogeneous or heterogeneous catalyst, e.g. a solid phase metal catalyst. The secondary carbonylation reaction may be a homogeneous reaction or a heterogeneous reaction. In one embodiment, the catalyst may be similar to the catalyst used for the carbonylation reaction in reaction zone 101, discussed further below. In another embodiment, the catalyst may be a liquid phase catalyst. Also, the reaction in the second reactor (and optionally that in the first reactor, as well) may be conducted in a counter-current or co-current manner, with a vapor phase co-current reaction being preferred. Although the catalyst for the reaction in the secondary reactors 111, 112 may be the same as the catalyst in the reaction zone 101, it is preferred that the catalyst in the secondary reactors 111, 112 are different from the catalyst in the reaction zone 101. Preferably, the catalyst in the secondary reactors 111, 112 is tailored to account for a carbon monoxide stream that comprises lower amounts of carbon monoxide. Preferably, the catalyst in the second reactor is a rhodium diiodide dicarbonyl anion that is ionically bound to a suitable resin, e.g., polyvinylpyridine or carbon.

The secondary reactors 111, 112, generally, may be any reactor suitable for carbonylation of methanol with a relatively low carbon monoxide feed stream. In preferred embodiments, the secondary reactors 111, 112 are each independently a trickle bed reactor and/or a fixed bed reactor. Trickle bed reactors and fixed bed reactors preferably comprise a solid phase metal catalyst fixed or packed in a catalyst bed. In one embodiment, each of the secondary reactors 111, 112 may comprise catalyst section 113 and a head space 114.

Derivative stream 108 fed to the secondary reaction zone 103 preferably comprises a relatively lower concentration of carbon monoxide than is fed to the carbonylation reaction zone 101. In one embodiment, the concentration of carbon monoxide in derivative stream 108 may be at least 5% lower than the concentration of the carbon monoxide fed to the reaction zone 101, e.g., at least 10% lower, at least 25% lower, or at least 50% lower. In other embodiments, the carbon monoxide concentration of derivative stream 108 (either in mol % or carbon monoxide partial pressure) may be at least 5% lower than the concentration in a conventional off-gas stream, e.g., at least 10% lower, at least 25% lower, or at least 50% lower. In one embodiment, because of the relatively low amount of carbon monoxide in the feed, the molar ratio of other reactants, e.g., methanol and/or methanol derivatives, to carbon monoxide in the second reactor is greater than 0.02:1, e.g., greater than 0.1:1, greater than 0.25:1 or greater than 0.5:1.

In preferred embodiments, the reactant, e.g., methanol and/or methanol derivatives, reacted in the secondary reactors 111, 112, may be present in derivative stream 108. In one embodiment, derivative stream 108 comprises methanol and/or methanol derivative in an amount ranging from 5 mol % to 90 mol %, e.g., from 25 mol % to 75 mol % or from 40 mol % to 60 mol %. In other embodiments, derivative stream 108 is in the vapor phase and has a methanol and/or methanol derivative partial pressure of from 10% to 90% of the total pressure of derivative stream 108, e.g., from 25% to 75% of from 40% to 60%. In preferred embodiments the methanol and/or methanol derivative reactant in secondary reactors 111, 112 is methyl acetate. In optional embodiments, fresh methanol and/or methanol derivatives may be fed to secondary reactors 111, 112, via line 115. In other optional embodiments, methanol and/or methanol derivatives contained in the optional derivative stream 110 from the separation zone 102 may be fed to secondary reactors 111, 112, as shown in FIGS. 1 and 2, respectively. In other embodiments, derivative stream 108 comprises acetaldehyde. In these embodiments, secondary reactor 111 may react the acetaldehyde in derivative stream 108 to form other materials. For example, the acetaldehyde may be reacted to form ethanol, which may then be converted to propionic acid, which is easily removed from the product stream. By converting the acetaldehyde in derivative stream 108, acetaldehyde is advantageously removed from derivative stream 108. This reaction of acetaldehyde lowers the amount of acetaldehyde in the product stream and lessens the need for subsequent acetaldehyde removal units, e.g., PRS units.

In FIG. 1, secondary reactor 111 preferably is a high pressure liquid phase carbonylation secondary reactor. The supplemental carbonylation reaction in the secondary reactor 111 may be conducted over a liquid-phase homogeneous catalyst or a solid heterogeneous catalyst. In one embodiment, the liquid-phase homogeneous catalyst comprises metal dissolved in a solution, e.g., rhodium and/or iridium dissolved in acetic acid. In one embodiment, the reaction in secondary reactor 111 is carried out at a pressure of from 0.1 MPa to 10 MPa, e.g., from 1 MPa to 5 MPa or from 2 MPa to 3 MPa and a temperature of from 100° C. to 350° C., e.g., 150° C. to 300° C. or 175° C. to 250° C. Secondary reactor 111 is preferably operated at lower pressure than that of the primary reactor. In one embodiment, secondary reactor 111 is operated at a temperature similar to that of the primary reactor. In other embodiment, secondary reactor 11 is operated at a temperature that is higher, e.g., at least 5% higher or at least 10% higher, than the temperature of the primary reactor.

Derivative stream 108 is preferably fed to secondary reactor 111 as a liquid or as a condensed vapor stream, optionally with fresh reactants 115, to produce a secondary crude product stream 116 that comprises acetic acid and overhead stream 117. Overhead stream 117 comprises methyl iodide, residual carbon monoxide, vaporized methanol, vaporized methyl acetate, and other non-condensable gases such as methane. Overhead stream 117 is condensed and fed to a knock-out pot 118 to remove a liquid stream 119 and a vapor stream 120. Liquid stream 119, along with optional derivative stream 110, is sprayed on the catalyst section 114 in secondary reactor 111.

Secondary crude product stream 116 may be processed further and fed to the separation zone 102 or may be combined with the purified acetic acid product 107. In some embodiments, secondary crude product stream 116 may be recovered independently of purified acetic acid product 107. Preferably, the secondary crude product stream 116 is enriched in acetic acid relative to derivative stream 108. In one embodiment, secondary crude product stream 116 comprises from 30 mol % to 95 mol % acetic acid, e.g., from 50 mol % to 75 mol % or from 45 mol % to 70 mol %. In terms of limits, secondary crude product stream 116 comprises at least 25 mol % acetic acid, e.g., at least 50 mol %, at least 40 mol % or at least 60 mol %. In terms of partial pressures, secondary crude product stream 116 (when in the vapor phase) may have an acetic acid partial pressure of from 30% to 95% of the total pressure of secondary crude product stream 116, e.g., from 50% to 75% or from 45% to 70%. In one embodiment, secondary crude product stream 116 may further comprise low amounts of carbon monoxide, e.g., less than 40 mol % carbon monoxide, e.g., less than 25 mol %, less than 10 mol %, less than 5 mol %, or less than 3 mol %. In other embodiments, secondary crude product stream 116 may further comprise methanol and/or methanol derivatives in an amount less than 50 mol %, e.g., less than 40 mol %, less than 25 mol % or less than 15 mol %. In terms of ranges secondary crude product stream 116 may comprise from 10 mol % to 50 mol % methanol and/or methanol derivative, e.g., from 10 mol % to 40 mol %, or from 15 mol % to 30 mol %.

Vapor stream 120 may be purged or flared as shown. In preferred embodiments, vapor stream 120 comprises substantially less carbon monoxide, and more preferably essentially no carbon monoxide, than derivative stream 108. In addition, a portion of vapor stream 120 may be fed to one or more recovery unit 121. As shown in FIG. 1, there is provided one recovery unit 121. A scrubbing solvent 122, preferably chilled to less than 25° C., may be fed to recovery unit 121 to scrub vapor stream 120 of low boiling point components, such as methyl iodide, which are removed via line 123 and are preferably returned to the reaction zone 101. Exemplary scrubbing solvents include methanol, methyl acetate, dimethyl ether, acetic acid and mixtures thereof. The overheads of recovery unit 121 may exited as purge gas 124.

In FIG. 2, secondary reactor 112 preferably is a low pressure gas phase carbonylation secondary reactor. The supplemental carbonylation reaction in the secondary reactor 112 may be reacted with a heterogeneous catalyst. In one embodiment, the reaction in the secondary reactor is carried out at a pressure of from 0.01 MPa to 10 MPa, e.g., 0.05 MPa to 5 MPa or 0.05 MPa to 1 MPa and a temperature of from 150° C. to 350° C., e.g., 150° C. to 300° C. or 175° C. to 250° C. By conducting the reaction in the secondary reactor at lower pressures, the burden on system components, e.g., pumps and compressors, may be reduced. Also, because lower temperature and/or lower pressure operation is less corrosive, vessels need not be made from expensive corrosion-resistant metals and less-expensive metals, e.g., standard stainless steel, may be used.

The derivative stream 108 is preferably fed to secondary reactor 112 as a vapor, optionally with derivative stream 110, to produce a secondary crude product stream 125. In optional embodiment, fresh reactants may be added to head space 114 of the secondary reactor 112. The secondary crude product stream 125 is condensed and fed to knock-out pot 126 to remove a liquid stream 127 comprising acetic acid and a vapor stream 128. Liquid stream 127 may be processed further and fed to the separation zone 102 or may be combined with the purified acetic acid product 107. In some embodiments, secondary crude product stream 125 may be recovered independently of purified acetic acid product 107. Preferably, liquid stream 127 is enriched in acetic acid relative derivative stream 108. In one embodiment liquid stream 127 comprises from 30 mol % to 95 mol % acetic acid, e.g., from 50 mol % to 75 mol % or from 45 mol % to 70 mol %. In terms of limits, stream 127 comprises at least 25 mol % acetic acid, e.g., at least 50 mol %, at least 40 mol % or at least 60 mol %. In one embodiment, stream 127 may further comprise low amounts of carbon monoxide, e.g., less than 40 mol % carbon monoxide, less than 25 mol %, less than 10 mol %, less than 5 mol %, or less than 3 mol %. In other embodiments, stream 127 may further comprise methanol and/or methanol derivatives in an amount less than 50 mol %, e.g., less than 40 mol %, less than 25 mol % or less than 15 mol %. In terms of ranges, stream 127 may comprise from 10 mol % to 50 mol % methanol and/or methanol derivative, e.g., from 10 mol % to 40 mol %, or from 15 mol % to 30 mol %.

In some embodiments, where the secondary reaction is conducted in the vapor phase, the reaction temperature may be maintained at a temperature below the dew point of acetic acid. In such cases, the resultant acetic acid product will contain an amount of rhodium. This amount of rhodium may be greater than the amount of rhodium, if any, in conventional acetic acid products that do not use the inventive processes and/or systems.

Vapor stream 128 in FIG. 2 may be purged or flared as shown. In preferred embodiments, vapor stream 128 comprises substantially less carbon monoxide, and more preferably comprises essentially no carbon monoxide, than derivative stream 108. In addition, a portion of vapor stream 128 may be fed to one or more recovery unit 121, as discussed above with reference to FIG. 1.

Figure 3:
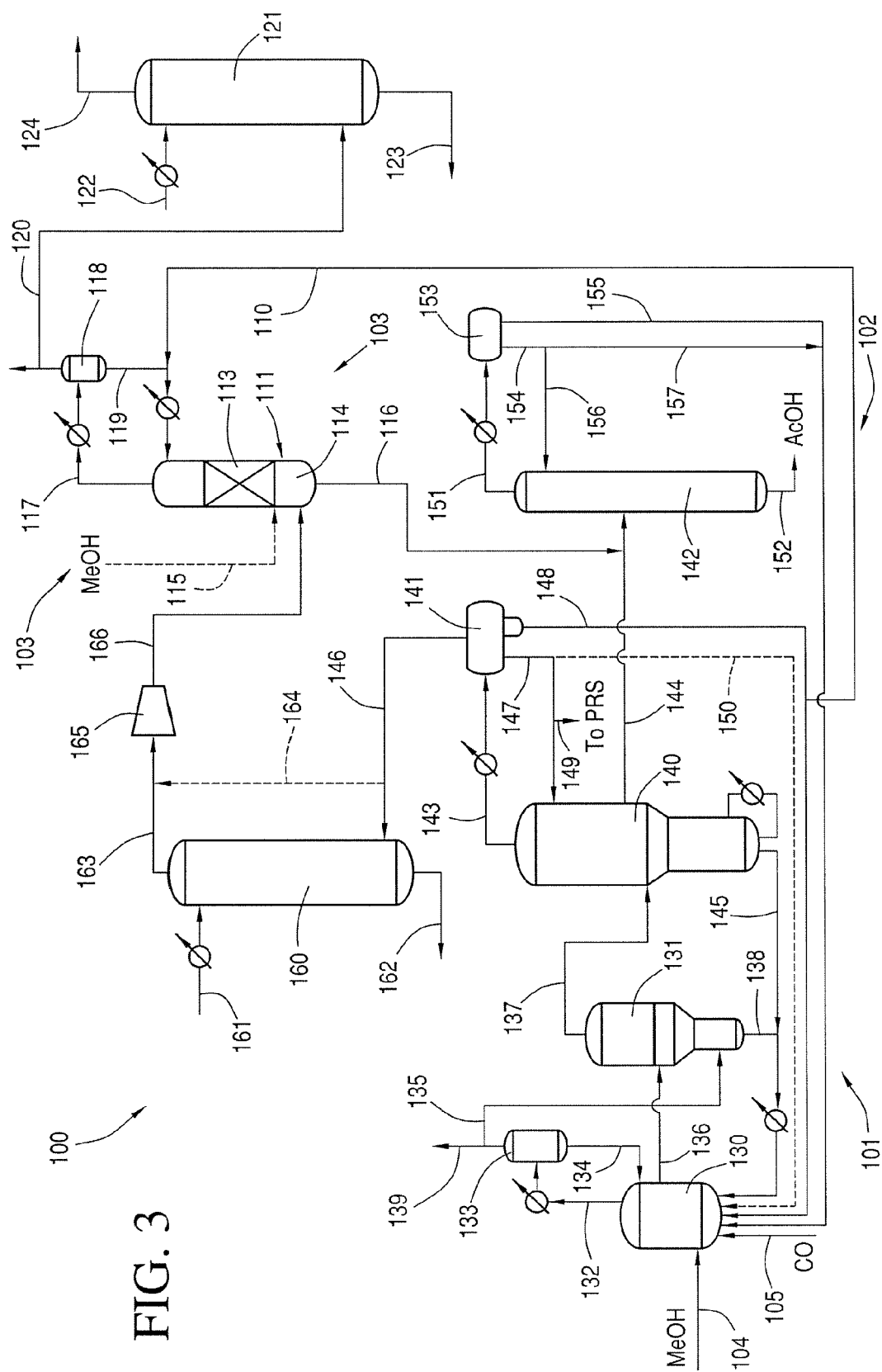
FIG. 3 is a detailed schematic diagram of an exemplary high pressure liquid phase carbonylation secondary reactor for processing a purged derivative stream from an acetic acid purification section in accordance with an embodiment of the present invention.
Figure 4:
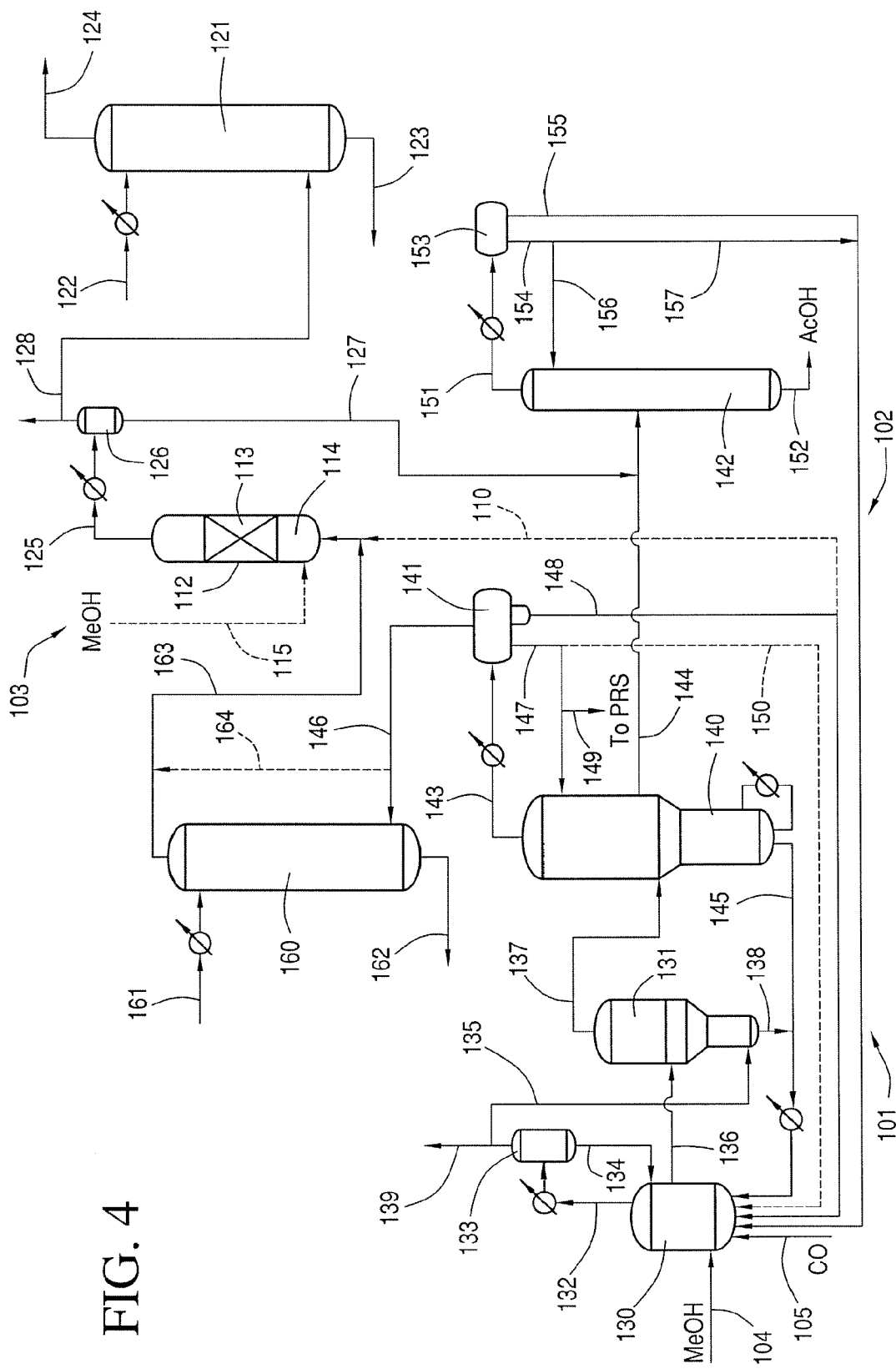
FIG. 4 is a detailed schematic diagram of an exemplary low pressure gas phase carbonylation secondary reaction for processing a purged derivative stream from an acetic acid purification section in accordance with an embodiment of the present invention.
Figure 5:
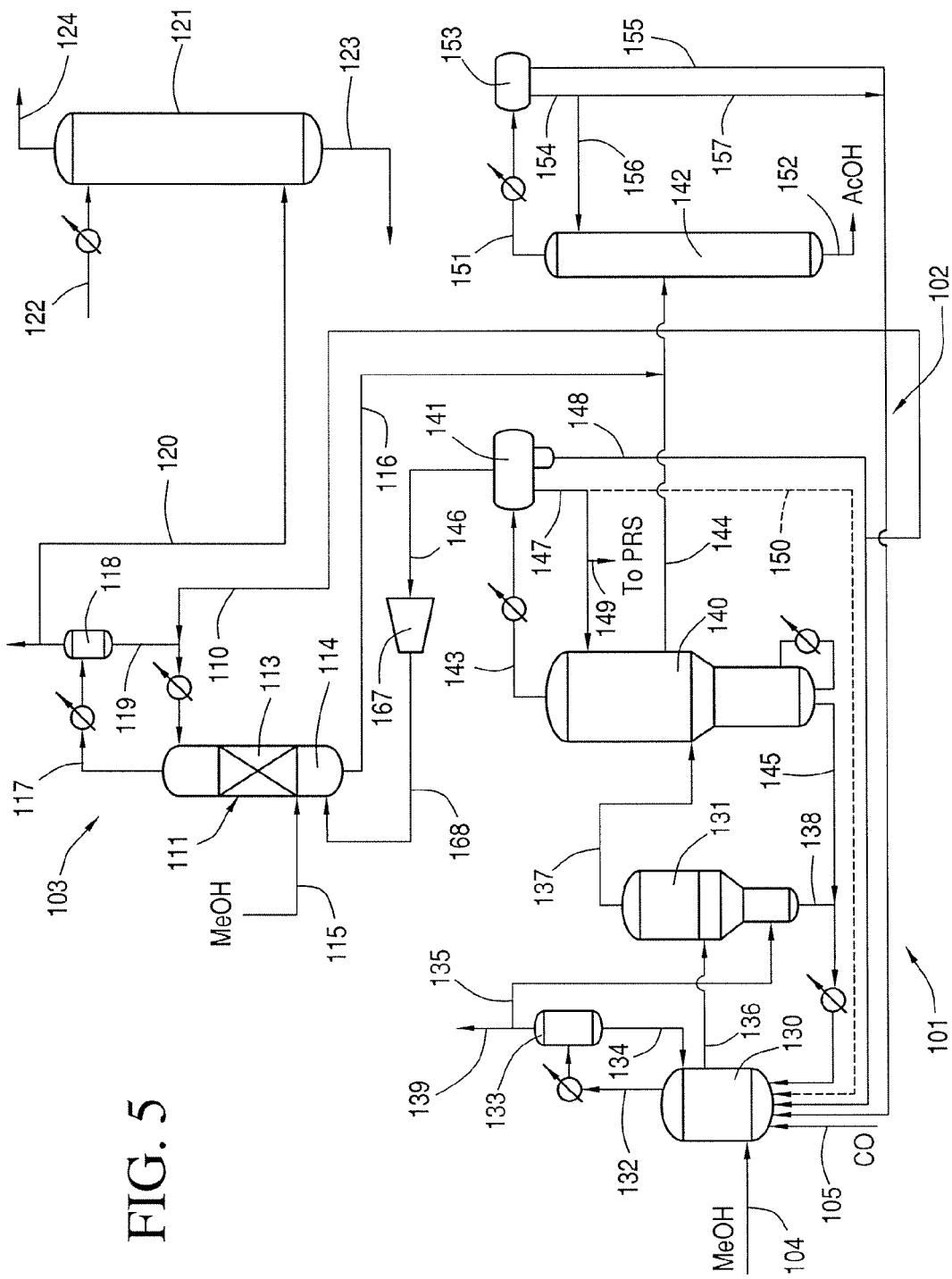
FIG. 5 is a schematic diagram of an exemplary acetic acid reaction process, which includes reaction and separation, in accordance with an embodiment of the present invention.

Returning to the reaction zone 101, an exemplary reaction zone 101 is shown in FIGS. 3-5. Reaction zone 101 comprises a first reactor 130, flasher 131 and a reactor recovery unit 132. In embodiments of the present invention the primary carbonylation reaction is conducted in the first reactor 130. The carbon monoxide feed stream 105 has a high carbon monoxide content relative to the derivative streams fed to secondary reaction zone 103. In one embodiment, the carbonylation is achieved by reacting carbon monoxide with methanol in the first reactor 130, e.g., a continuous stirred tank reactor ("CSTR"). When using a CSTR, the catalyst is dissolved in the reaction solvent and liquid methanol and carbon monoxide gas are injected from the bottom as reaction raw materials and made to react with one another. When a CSTR is utilized, the CSTR may be adapted to agitate the reaction solution by an agitation device such as an impeller. Alternatively, a bubble column reactor may be utilized as the first reactor to perform the carbonylation. When a bubble column reactor is utilized, a cylindrical reactor is filled with a reaction solvent and a solid catalyst. Liquid methanol is supplied from the bottom as reaction raw material while carbon monoxide gas is injected upward from the bottom as jet stream. The injected carbon monoxide gas forms bubbles as it rises in the liquid contained in the cylindrical reactor and particles of the catalyst are also driven to move upward in the cylindrical reactor by the gas lift effect and dispersed into the liquid. As one example, the carbon monoxide may be injected into the liquid contained in a cylindrical reactor as jet stream by way of a nozzle arranged at the bottom of the cylindrical reactor for the purpose of mobilizing particles of the solid catalyst in the reactor, as disclosed in Japanese Patent Application Laid-Open No. 6-340242, which is hereby incorporated by reference in its entirety. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference in its entirety.

The present invention may be appreciated in connection with, for example, the carbonylation of methanol with carbon monoxide in a homogeneous catalytic reaction system comprising a reaction solvent, methanol and/or reactive derivatives thereof, a Group VIII catalyst, at least a finite concentration of water, and optionally an iodide salt.

Suitable Group VIII catalysts include rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauß, et al., *Applied Homogeneous Catalysis with Organometallic Compounds: A Comprehensive Handbook in Two Volume*, Chapter 2.1, p. 27-200, (1$^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, the entireties of which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

An alkyl halide co-catalyst/promoter is generally used in combination with the Group VIII metal catalyst component. Methyl iodide is preferred as the alkyl halide promoter. Preferably, the concentration of alkyl halide in the liquid reaction composition is in the range of 1 to 50% by weight, preferably 15 to 25% by weight.

The halogen promoter may be combined with a salt stabilizer/co-promoter compound, which may include salts of a metal of Group IA or Group IIA, a quaternary ammonium, phosphonium salt or mixtures thereof. Particularly preferred are iodide or acetate salts, e.g., lithium iodide or lithium acetate.

Other promoters and co-promoters may be used as part of the catalytic system of the present invention as described in U.S. Pat. No. 5,877,348, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in the first reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa Acetic acid is typically manufactured in a liquid phase reaction at a temperature of from about 150-200° C. and a total pressure of from about 2 to about 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Methanol feed stream 104 preferably comprises methanol and/or reactive derivatives thereof. Suitable reactive derivatives of methanol include methyl acetate, dimethyl ether, and methyl formate. In one embodiment, a mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range of from 0.5 wt. % to 70 wt. %, e.g., from 0.5 wt. % to 50 wt. %, from 1 wt. % to 35 wt. %, or from 1 wt. % to 20 wt. %.

Carbon monoxide feed stream 105 may be essentially pure or may contain small amounts of inert impurities such as carbon dioxide, methane, nitrogen, noble gases, water and $C_1$ to $C_4$ paraffinic hydrocarbons. Carbon monoxide feed stream 105 preferably comprises a high content of carbon monoxide, e.g., at least 95 mol %, at least 98 mol %, or at least 99 mol %. Carbon monoxide feed stream 105 may also be characterized in terms of partial pressure. Thus, carbon monoxide feed stream 105 may have a carbon monoxide partial pressure of at least 95% of the total pressure of carbon monoxide feed stream 105, e.g., at least 98% or at least 99%. Hydrogen may be generated in the carbon monoxide feed stream by the water gas shift reaction. Preferably, the partial pressure of hydrogen is maintained at a low level, for example, less than 0.1 MPa or less than 0.05 MPa, as its presence may result in the formation of various hydrogenation products. The partial pressure of carbon monoxide in the reaction is suitably in the range of from 0.1 MPa to 7 MPa, e.g., from 0.1 MPa to 3.5 MPa, or from 0.1 MPa to 1.5 MPa.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range of from 0.1 wt. % to 16 wt. %, e.g., from 1 wt. % to 14 wt. %, or from 1 wt. % to 10 wt. %.

In accordance with a preferred carbonylation process according to the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed with gaseous carbon monoxide bubbled through an acetic acid solvent reaction medium containing the catalyst e.g., rhodium or iridium, methyl iodide promoter, methyl acetate, and/or additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt % to 30 wt. %, e.g., from 1 wt. % to 25 wt. %, or from 2 wt. % to 20 wt. %; and the lithium iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

First reactor 130 is preferably either a stirred vessel, e.g., CSTR, or bubble-column type vessel, with or without an agitator, within which the reaction medium is maintained, preferably automatically, at a predetermined level. This predetermined level may remain substantially constant during normal operation. Into first reactor 130, methanol, carbon monoxide, and sufficient water may be continuously introduced as needed to maintain at least a finite concentration of water in the reaction medium.

In one embodiment, carbon monoxide, e.g., in the gaseous state, is continuously introduced into first reactor 130, desirably below the agitator, which is used to stir the contents. The temperature of first reactor 130 may be controlled, as indicated above. Carbon monoxide feed 105 is introduced at a rate sufficient to maintain the desired total reactor pressure.

The gaseous feed is preferably thoroughly dispersed through the reaction medium by the stirring means. Gaseous purge is desirably vented via off-gas line 132 from first reactor 130. Off-gas vent 132 prevents buildup of gaseous by-products, such as methane, carbon dioxide, and hydrogen, and to maintain a set carbon monoxide partial pressure at a given total reactor pressure. Off-gas vent 132 is not a derivative stream, as discussed above. As shown in FIGS. 3-5, a reactor recovery unit 133 may be utilized to remove low boiling point components from the vented gas in line 132. The gaseous purge streams from first reactor 130 may be combined or scrubbed separately and are typically scrubbed with either acetic acid, methanol, or mixtures of acetic acid and methanol to prevent loss of low boiling components such as methyl iodide from the process. If methanol is used as the vent scrub liquid solvent, the enriched methanol (containing methyl iodide) from reactor recovery unit 133 is typically returned to the process, e.g., via line 134, although it can also be returned into any of the streams that recycle back to the reactor such as the flasher residue or light ends or dehydration column overhead streams. If acetic acid is used as the vent scrub liquid solvent, the enriched acetic acid (containing methyl iodide) from the scrubber is typically stripped of absorbed light ends and the resulting lean acetic acid is recycled back to the scrubber (not shown). The light end components stripped from the enriched acetic acid scrubbing solvent may be returned to the main process directly, e.g., via line 134, or indirectly in several different locations including the first reactor 130, flasher 131, e.g., via line 135, or a suitable area in the separation zone 102. In one embodiment, the stream exiting the top of reactor recovery unit 133 is exited via line 139 to further processing, which may entail, for example, further separation or scrubbing. Preferably, the contents of line 136, which may contain, inter alia, (residual) carbon monoxide and methanol, may be further reacted, preferably in secondary reaction zone 103, to produce additional acetic acid. Optionally, the gaseous purge streams may be vented through the flasher base liquid or lower part of the light ends column to enhance rhodium stability and/or they may be combined with other gaseous process vents (such as the purification column overhead receiver vents) prior to scrubbing.

The crude acetic acid product comprises an amount of unreacted carbon monoxide. As noted above, in some embodiments, the acetic acid in the crude acetic acid product is separated into purified acetic acid and at least one, e.g., at least two or at least three, derivative streams. In preferred embodiments, at least one, e.g., at least two or at least three, of these derivative streams comprises the residual carbon monoxide. The derivative stream comprising residual carbon monoxide may be beneficially further reacted to form additional acetic acid.

The crude acetic acid product is drawn off from the first reactor 130 at a rate sufficient to maintain a constant level therein and is provided to flasher 131 via stream 136. In flasher 131, the crude product is separated in a flash separation step to obtain a volatile ("vapor") overhead stream 137 comprising acetic acid and a less volatile stream 138 comprising a catalyst-containing solution. The catalyst-containing solution comprises acetic acid containing the rhodium and the iodide salt along with lesser quantities of methyl acetate, methyl iodide, and water. The less volatile stream 138 preferably is recycled to reactor 130. Vapor overhead stream 137 also comprises methyl iodide, methyl acetate, water, PRCs. Dissolved and/or entrained gases exit first reactor 130 and enter flasher 131 comprise a portion of the carbon monoxide and may also contain gaseous by-products such as methane, hydrogen, and carbon dioxide. The dissolved gases exit the flasher 131 as part of overhead stream 137. In some embodiments, the low-boiling overhead vapor stream 137 may be fed to the secondary reaction zone 103, e.g., to the secondary reactor.

Overhead stream 137 from flasher 131 is directed to separation zone 102. Separation zone 102 comprises light ends column 140, decanter 141, and drying column 142. Additionally, separation zone 102 may also comprise one or more columns for removing permanganate reducing compounds ("PRCs"), guard beds, heavy ends columns, extractors, etc.

In light ends column 140, stream 137 yields a low-boiling overhead vapor stream 143, a purified acetic acid product that preferably is removed via a side stream 144, and a high boiling residue stream 145. Acetic acid removed via side stream 144 preferably is subjected to further purification, such as in drying column 142 for selective separation of acetic acid from water and/or an optional heavy ends column (not shown), as described in U.S. Pat. No. 6,627,770, the entirety of which is hereby incorporated by reference. Preferably, side stream 144 and residue stream 145 comprise substantially no carbon monoxide or no detectable amounts of carbon monoxide.

The low-boiling overhead vapor in line 143 may comprise dissolved and/or entrained carbon monoxide; methyl iodide; methyl acetate; hydrogen; water; PRCs; acetic acid; inerts such as nitrogen, argon, and helium; and other dissolved gases. In terms of upper limits, the low-boiling overhead vapor in line 143 may comprise less than 75 mol % carbon monoxide, e.g., less than 60 mol %; less than 50 mol %, or less than 40 mol %; and/or may have a carbon monoxide partial pressure less than 75% of the total pressure of the low-boiling overhead vapor, e.g., less than 60%, less than 50%, or less than 40%. Preferably, the amount of dissolved and/or entrained carbon monoxide in line 143 preferably is less than the amount of carbon monoxide in feed stream 105, e.g., at least 5% less, at least 10% less, at least 25% less, or at least 50% less. In terms of ranges, the amount of carbon monoxide in line 143 may range from 10 mol % to 75 mol %, e.g., from 25 mol % to 60 mol %, or from 40 mol % to 50 mol %; or the carbon monoxide partial pressure may range from 10% to 75% of the total pressure of low-boiling overhead vapor, e.g., from 25% to 60% of from 40% to 50%. Preferably, the low-boiling overhead vapor in line 143 comprises at least 0.1 mol % carbon monoxide, e.g., at least 0.5 mol %, or at least 1; and/or has a carbon monoxide partial pressure of at least 0.1% of the total pressure of the low-boiling overhead vapor, e.g., at least 0.5% or at least 1%. Also, the low-boiling overhead vapor in stream 143 may comprise at least 0.1 mol % methyl iodide, e.g., at least 1 mol %, or at least 5 mol %. In terms of ranges, stream 143 may comprise from 0.1 mol % to 30 mol % methyl iodide, e.g., from 1 mol % to 25 mol %, or from 5 mol % to 20 mol %. In some embodiments, the derivative stream of the crude acetic acid product in line 143 may be fed to the secondary reaction zone 103.

It has been disclosed in U.S. Pat. Nos. 6,143,930 and 6,339,171 that there is generally a higher concentration of PRCs, and in particular acetaldehyde, in the low-boiling overhead vapor stream 143 exiting the light ends column 140 than in the high-boiling residue stream 145. In some embodiment, low-boiling overhead vapor stream 140, containing PRCs, optionally may be subjected to additional processing in a PRC removal system ("PRS") (not shown) to reduce and/or remove the amount of PRCs present (or a portion thereof). PRCs are formed during the carbonylation of methanol in the presence of a Group VIII metal carbonylation catalyst. PRCs, may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

As shown, low-boiling overhead vapor stream 143, is preferably condensed and directed to an overhead phase separation unit, as shown by overhead receiver decanter 141. Conditions are desirably maintained in the process such that low-boiling overhead vapor stream 143, once in decanter 141, will separate into a light phase and a heavy phase. Generally, low-boiling overhead vapor stream 143 is cooled to a temperature sufficient to condense and separate the condensable methyl iodide, methyl acetate, acetaldehyde and other carbonyl components, and water into two phases. A gaseous portion of stream 143 may include carbon monoxide, and other noncondensable gases such as methyl iodide, carbon dioxide, hydrogen, and the like and is vented from the decanter 141 via line 146. Line 146 preferably has a partial pressure of carbon monoxide of less than 95% of the total pressure of line 146, e.g., less than 80%; less than 75%; less than 60%; less than 50%; or less than 40%. As used herein, all partial pressures are based upon the total pressure of all non-condensable components in the specified stream or vessel. Additionally or alternatively, line 146 may comprise less than 95 mol % carbon monoxide, e.g., less than 80 mol %; less than 75 mol %; less than 60 mol %; less than 50 mol %; or less than 40 mol %. Line 146 preferably has a carbon monoxide partial pressure and/or a weight percentage that is lower than carbon monoxide feed stream 105, which feeds first reactor 130, e.g., 5% lower; 10% lower; 25% lower or 50% lower. In terms of ranges, the amount of carbon monoxide in line 146 optionally ranges from 10 mol % to 95 mol %, e.g., from 25 mol % to 75 mol %, or from 40 mol % to 60 mol %. Optionally, line 146 has a carbon monoxide partial pressure of from 10% to 95% of the total pressure of line 146, e.g., from 25% to 75% or from 40% to 60%. Line 146 preferably has a mole percentage of methyl acetate that optionally ranges from 10 mol % to 60 mol %, e.g., from 15 mol % to 50 mol %, or from 25 mol % to 45 mol %; and/or a methyl acetate partial pressure of from 10% to 60% of the total pressure of line 146, e.g., from 15% to 50% or from 25% to 45%. This derivative stream in line 146 comprising carbon monoxide may be directed to a secondary reaction zone 103, for reaction with methanol to form additional acetic acid, as discussed above in FIGS. 1 and 2.

The condensed light phase 147 in decanter 141 preferably comprises water, acetic acid, and PRCs, as well as quantities of methyl iodide and methyl acetate. The condensed heavy phase 148 in decanter 141 will generally comprise methyl iodide, methyl acetate, and PRCs. The condensed heavy liquid phase 148 in the decanter 141 can be conveniently recirculated, either directly or indirectly, to the reactor 130. For example, a portion of this condensed heavy liquid phase 148 can be recirculated to the reactor, with a slip stream (not shown), generally a small amount, e.g., from 5 to 40 vol. %, or from 5 to 20 vol. %, of the heavy liquid phase being directed to a PRS. This slip stream of the heavy liquid phase 148 may be treated individually or may be combined with the condensed light liquid phase 147 for further distillation and extraction of carbonyl impurities in accordance with one embodiment of the present invention.

As shown in FIGS. 3-5, the light phase exits decanter 141 via stream 147. A first portion, e.g., aliquot portion, of light phase stream 147 may be recycled to the top of the light ends column 140 as a reflux stream. A second portion, e.g., aliquot portion, of light phase stream 147 may be directed to the optional PRS (not shown), e.g., as shown by stream 149. A third portion, e.g., aliquot portion, of the light phase stream 147 optionally may be recycled to reactor 130, e.g., as shown by optional recycle stream 150, when additional water is desired or needed in reactor 130. In preferred aspects the water level in the reactor is maintained at a desired level without recycling stream 150 to reactor 130 since recycling stream 150 to the reactor 130 undesirably will result in the recycle of acetic acid and unnecessarily increasing the load on reactor 130.

Light ends column 140 also preferably forms a residuum or bottoms stream 145, which comprises primarily acetic acid and water. Since light ends bottoms stream 145 typically will comprise some residual catalyst, it may be beneficial to recycle all or a portion of the light ends bottoms stream 145 to reactor 130, as shown by optional line 150. Preferably, the light ends bottoms stream 145 may be combined with catalyst phase 138 from flasher 131 and returned together to reactor 130.

As indicated above, in addition to the overhead phase, the light ends column 140 also forms an acetic acid side stream 144, which preferably comprises primarily acetic acid and water. Optionally, a portion of side stream 144 may be recirculated to the light ends column, preferably to a point below where side stream 144 was removed from light ends column, as described in US Pub. No. 2008/0287706, the entirety of which is hereby incorporated by reference.

Since side stream 144 contains water in addition to acetic acid, side stream 144 from the light ends column 140 preferably is directed to a drying column 142, in which the acetic acid and water are separated from one another. As shown, drying column 142, separates acetic acid side stream 144 into an overhead stream 151 comprised primarily of water and a bottoms stream 152 comprised primarily of purified, dried acetic acid. Overhead stream 151 preferably is cooled and condensed in a phase separation unit, e.g., decanter 153, to form a light phase 154 and a heavy phase 155. As shown, a portion of the light phase 154 is refluxed, as shown by stream 156 and the remainder of the light phase is returned to the reactor 130, as shown by stream 157. The heavy phase, which typically is an emulsion comprising water and methyl iodide, preferably is returned in its entirety to the reactor 130, as shown by stream 155, optionally after being combined with stream 157, although a portion may also be further processed (not shown).

The drying column bottoms stream 152 preferably comprises or consists essentially of acetic acid. In preferred embodiments, the drying column bottoms stream comprises acetic acid in an amount greater than 90 mol %, e.g., greater than 95 mol % or greater than 98 mol %. Optionally, the drying column bottoms stream 152 may be further processed, in a heavy ends column (not shown) or iodide guard bed (not shown), prior to being stored or transported for commercial use. Of course, the separation systems of FIGS. 3-5, are merely examples of separation schemes that may be utilized in the present invention. Other combinations of separation units may just as easily be utilized. Preferable separation systems are those wherein at least a portion of residual carbon monoxide is separated and/or recovered from the crude acetic acid product.

Returning to vent gas stream 146 from the overhead decanter 141 of the light ends column 140. In a preferred embodiment, vent gas stream 146, which comprises an amount of residual carbon monoxide, may be directed to secondary reaction zone 103. In FIGS. 3 and 4, the vent gas stream 146 is initially processed in a recovery unit 160 to remove any low boiling point compounds, such as methyl iodide.

A scrubbing solvent 161, preferably chilled to less than 25° C., may be fed to recovery unit 160 to scrub vapor stream 146 of low boiling point components, such as methyl iodide, which are removed via line 162 and are preferably returned to the reaction zone 101. Scrubbing solvents include methanol, methyl acetate, dimethyl ether, acetic acid and mixtures thereof. The overheads of recovery unit 160 may exited as purge gas 163. In one optional embodiment, a portion of the vent gas stream 146 may by-pass the recovery unit 160 in line 164 and be combined with the overhead vapor 163.

The purge gas 163 exiting the top of recovery unit 160 comprises carbon monoxide, methyl acetate, and optionally methyl iodide. In preferred embodiments, purge gas 163 passes through compressor 165 to form a high pressure derivative stream 166. In preferred embodiments, the total pressure of the vapor in high pressure derivative stream 166 is from 0.1 MPa to 10 MPa, e.g., 0.5 MPa to 5 MPa or 0.5 MPa to 2 MPa. In one embodiment, the purge gas comprises substantially no methyl iodide, which has been removed by the recovery unit 160. The high pressure derivative stream 166 is fed to the secondary reaction zone 103 in FIG. 3. The secondary reaction zone 103 comprises the secondary reactor 111 as described above in FIG. 1. The secondary crude product stream 116 is returned to separation zone 102 and co-fed with the side stream 144 to drying column 142. A derivative stream 110 from the heavy phase stream 148 may be also fed to the secondary reactor 111 with the liquid stream 119.

In FIG. 4, the vent gas stream 146 from the overhead decanter 141 passes through the recovery unit 160 to generate a purge gas 163. In one embodiment, purge gas 163 does not pass through a compressor and remains at a relatively lower pressure than high pressure derivative stream 166 in FIG. 3. Purge gas 163 is fed to secondary reaction zone 103 of FIG. 4. The secondary reaction zone 103 comprises the secondary reactor 112 as described above in FIG. 2. Optionally, along with the purge gas 163, fresh reactants in line 115 and derivative stream 110, may also be fed to secondary reactor 112. Secondary reactor 112 generates a secondary crude product stream 125 that is condensed and fed to a knock-out pot 126 to remove a liquid stream 127 comprising acetic acid. Liquid stream 127 is returned to separation zone 102 and co-fed with the side stream 144 to drying column 142.

In FIG. 5, vent gas stream 146 is fed to secondary reaction zone 103. In one embodiment, vent gas stream 146 from the overhead decanter 141 may pass through a compressor 167 to form a high pressure derivative stream 168 that is fed directly to a secondary reactor 111 as taught in FIG. 5. In preferred embodiments, the total pressure of the vapor in high pressure derivative stream 168 is from 0.1 MPa to 10 MPa, e.g., 0.5 MPa to 5 MPa or 0.5 MPa to 2 MPa. High pressure derivative stream 168 may comprise a higher amount of methyl iodide relative to the high pressure derivative stream 166 taught in FIG. 3. In alternative embodiments, the vent gas stream 146 may be fed as the derivative stream to a secondary reactor, without being compressed or processed in a recovery unit.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid, comprising:
contacting at least one of a carbonylation reaction stream and a derivative thereof comprising from 25 mol % to 75 mol % carbon monoxide with at least one of methanol and a methanol derivative over a metal catalyst to produce an acetic acid composition.

2. The process of claim 1, wherein a product stream comprises less than 40 mol % carbon monoxide.

3. The process of claim 1, wherein the carbon monoxide feed stream has been separated to remove condensable liquids.

4. The process of claim 1, wherein the metal catalyst comprises a solid catalyst.

5. The process of claim 1, wherein the metal catalyst comprises a liquid catalyst.

6. The process of claim 1, wherein the metal catalyst is a solid and comprises at least one metal selected from the group consisting of rhodium, iridium, ruthenium, nickel, and cobalt.

7. The process of claim 1, wherein the at least one of methanol and a methanol derivative is methyl acetate.

8. A process for producing acetic acid, the process comprising:
contacting a carbon monoxide feed stream comprising carbon monoxide and having a carbon monoxide partial pressure of less than 95% of the total pressure of the carbon monoxide feed stream with at least one of methanol and a methanol derivative over a solid phase metal catalyst to produce an acetic acid composition,
wherein the carbon monoxide feed stream is a carbonylation reaction product stream or a derivative thereof.

9. The process of claim 8, wherein the carbon monoxide feed comprises a carbon monoxide partial pressure less than 90% of the total pressure of the carbon monoxide feed stream.

10. A process for producing acetic acid, the process comprising:
contacting a carbon monoxide feed and at least one of methanol and a methanol derivative under conditions effective to produce an acetic acid product, wherein the overall conversion of carbon monoxide is greater than 90%,
wherein the carbon monoxide feed stream is a carbonylation reaction product stream or a derivative thereof.

11. The process of claim 1, wherein the contacting occurs in a secondary reactor; and wherein the process further comprises:

deriving the at least one of a carbonylation reaction stream and a derivative thereof from a crude acetic acid product formed by reacting carbon monoxide and at least one of methanol and a methanol derivative in a primary reactor.

12. The process of claim 11, wherein the deriving comprises:
flashing the crude acetic acid product into a first vapor stream comprising acetic acid and residual carbon monoxide and a first liquid residue stream comprising catalyst which is recycled to the first reactor; and
separating the flashed vapor stream into a second vapor stream comprising carbon monoxide, a purified acetic acid product, and a second liquid residue stream;
wherein the at least one of a carbonylation reaction stream and a derivative thereof comprises at least a portion of the second vapor stream or a derivative thereof.

13. The process of claim 12, further comprising:
decanting the second vapor stream to form a third vapor stream comprising residual carbon monoxide and a third liquid residue stream comprising methyl iodide, methyl acetate, acetaldehyde;
wherein the at least one of a carbonylation reaction stream and a derivative thereof comprises at least a portion of the third vapor stream or a derivative thereof.

* * * * *